United States Patent [19]

Gracovetsky

[11] Patent Number: 4,655,227

[45] Date of Patent: Apr. 7, 1987

[54] EQUIPMENT FOR THE DETECTION OF MECHANICAL INJURIES IN THE LUMBAR SPINE OF A PATIENT, USING A MATHEMATICAL MODEL

[75] Inventor: Serge Gracovetsky, St-Lambert, Canada

[73] Assignee: Diagnospine Research Inc., St-Lambert, Canada

[21] Appl. No.: 742,036

[22] Filed: Jun. 6, 1985

[51] Int. Cl.⁴ .............................................. A61B 5/10
[52] U.S. Cl. .................................... 128/781; 128/782
[58] Field of Search ................................ 128/781, 782

[56] References Cited

U.S. PATENT DOCUMENTS

2,532,915 12/1950 Horner ................................ 128/781
4,108,164 8/1978 Hall ..................................... 128/781

Primary Examiner—Carroll B. Dority, Jr.
Attorney, Agent, or Firm—Robic, Robica & Associates

[57] ABSTRACT

A method and equipment for the detection of mechanical injuries in the lumbar spine of a patient and the identification of these injuries, using a mathematical model applicable to the five lumbar vertebrae of a human being, and to to their disks. According to this method, the electromyographis (EMG) activities of the erectores and abdominals of the patient are measured in the bilateral and symmetrical manner with respect to the spine of the patient while the same is flexing forward in the mediane plane and pulling up a small load. The angle of flexion of the patient is measured during this flexion and is supplied as variable input to the mathematical model. A computer is used to run the model with its variable input in order to calculate the EMG activites of the erectores and abdominals that would normally be used by a healthy person to produce the same task. The so calculated EMG activities are then compared to the EMG activities actually measured on the patient and the parameters of the models are tuned to fit the calculated EMG activites for those measured on the patient. The amount and type of tuning that are necessary to complete the last step, are sufficient in practice to detect and identify the mechanical injuries that may be present in the lumbar spine of the patient.

13 Claims, 19 Drawing Figures

EQUIPMENT FOR THE DETECTION OF MECHANICAL INJURIES IN THE LUMBAR SPINE OF A PATIENT, USING A MATHEMATICAL MODEL

BACKGROUND OF THE INVENTION

1. Field of the Invention

The present invention relates to a method and to an equipment for the detection of mechanical injuries in the lumbar spine of a patient and for the identification of these injuries using a mathematical model representative of the physiological behavior of the spine of a human being.

2. Brief Description of the State of the Art

It is well known in the medical art that common back disorders have a mechanical etiology. It is also well known from pathological studies that there are two common patterns of disc injury which correspond to two different types of mechanical failure of the spine.

The first type of common injury hereinafter referred to as "compression injury", usually starts by a central damage to the disk with fracture of varying magnitude of the end plates of the adjacent vertebrae, sometimes followed by injection of part of the nucleus into the vertebral body. In this particular case, the injured end plate permits the invasion of the avascular nucleus and of the avascular inner portion of the annulus by granulation tissue ingrowing through the fractured end plate, such an invasion leading to gradual destruction of the avascular nucleus and inner annulus. In the early stages, the facet joints of the vertebrae are not affected and the outer annulus survives while the center portion of the disc is destroyed. With progression, the disc loses its thickness while the outer layer of the annulus remains relatively well preserved. With lost of disk thickness, the facet joint subluxates and develops a moderate degree of osteoarthritis.

Usually, the fracture of the end plate of a vertebra is an undisplaced fracture of cancellous bone which heals rapidly. The symptoms are short lived, typically lasting two weeks. The facet joint arthritis appears late. At this stage, symptoms may also arise from the reduction in size of the spinal canal (lateral or central spinal stenosis).

The other type of common injury hereinafter referred to as "torsional injury", is characterized by a damage to the annulus occuring simultaneously with a damage to the facet joints. The annulus is avulsed from the end plate and its laminae become separated while the central disk and the end plate remain intact. At the later stage, the annulus develops radial fissures while the nucleus remains relatively untouched. The changes in the facet joints are severed with massive joint destruction and osteophytosis similar to hypertropic arthritis. Relatively late in the process, there may be changes in the end-plates and central disks, with consequent collapse of the articular surfaces and chronic synovitis.

In this particular case, the basis injury is to collageneous ligamentaous tissue which requires six weeks to regain 60% of its strength. Because the injury involves both the disk and facet joints, it is more difficult for the joint to stabilize itself and recurrence is frequent. The condition is progressive and may lead to spinal stenosis, instability and degenerative spondilolisthesis.

Tests conducted in laboratory have shown that a compression injury is easily produced by compressing a joint between 2 Mpa to 6 Mpa. A torsional injury can be seen with as little as 2 to 3 degrees of forced rotation requiring only 22 to 33 Newton-meters of torque.

Statistically, in a group of patients suffering from back disorders, 64% exhibit torsional injuries whereas 35% exhibit axial compression injuries. Statistics have also shown that torsional injury occurs mainly at the $L_4$-$L_5$ level (almost 76% of forth joint problems are of torsional nature). Statistics have also shown that almost 98% of the compression injuries occur at the $L_5$-$S_1$ level. Statistics have further shown that double injuries where the joint is injured both in compression and torsion, occur in 22% of the cases, invariably at the $L_5$-$S_1$ level.

The following Table I reflects the probabilities of injuries among patients complaining from backache and sciatica, or sciatica alone. As can be seen from this Table, the important frequency of torsional injury cannot be overlooked. As can also be seen, the probability of a third type of injury giving symptoms is very remote.

TABLE I

| CLINICAL DETERMINATION OF THE VARIOUS PROBABILITIES OF INJURIES | | | |
|---|---|---|---|
| JOINT | P (injury) | P (compression) | P (torsion) |
| $L_5/S_1$ | 47% | 98% | 22% |
| $L_4/L_5$ | 47% | 1%< | 76% |
| $L_3/L_4$ | 5%< | 1%< | 1%< |
| $L_2/L_3$ | 1%< | 1%< | 1%< |
| $L_1/L_2$ | 1%< | 1%< | 1%< |
| | 100% | 100% | 100% |

It is also well known that health professionals are trained to use symptoms in the determination of diagnoses, the large numbers of known symptoms being quite naturally associated with a large number injuries and diagnoses. Unfortunately, as can be understood from the above short description of the pathology in the case of back disorders, both the compression and torsion injuries give rise to identical symptomology. Hence, symptoms cannot be used to diagnose a type of injury because identical symptoms may arise from different injuries.

It is also well known in the art that low back pain is the leading cause of disability in North America today, affecting from 8 to 9 million people. It is the most common disability in persons under the age of 45 and the third only after arthritis and heart disease in those over 45. It is also estimated that two of three persons will have a low back pain at some time of their lifes, usually between the ages of 20 and 50. The fact that problems are so common in people of working age is not coincidental. Indeed, most of the back problems are work-related. As the injury caused by a certain task cannot be identified from the patient's symptoms, it is of course not possible to relate directly a given task to an injury mode, although such a relationship is central to the definition of tasks that will not injure a specific worker.

The economic effects of back pain and injuries are staggering. Back problems are second only to the common cold as a cause of absenteism in the industry. It is moreover responsible for 93 million lost workdays every year and is a leading cause of reduced work capacity. Hence, an incentive for prevention of back injury is very large.

In order to unequivocally relate a given task to a given injury in the absence of any measurement of the effect of the task on a given joint, it has already been suggested to use mathematical and/or biomechanical model of spine, like the one suggested by J. M. Morris et al in their article "The Role of trunk in stability of the spine, J. Bone and Joint Surg., 43A, 1961. However, a major problem with the known models of spine, including the widely used model of J. M. Morris et al, is that they do not truly reflect the physiological behaviour of the spine over the full range of capacity.

Thus, by way of example, the model of J. M. Morris et al which assumes, as fundamental hypothesis, that the moment generated by the body weight and any external load carried by the patient is balanced by the combined action of the erectores spinae and the intra-abdominal pressure, is a very poor representation of physiological behaviour which is not supported by observations. By way of example, such a model predicts a total failure of the spinal mechanism at about one fourth of the known potential of a healthy spine.

The major reason why all of the models known to the inventor are defective is essentially because they give an incomplete representation of the actual anatomy of a human being. It is true that a moment-supporting member is required in such a model but this cannot be the abdominal pressure only, as suggested by J. M. Morris et al.

SUMMARY OF THE INVENTION

An object of the present invention is to provide a method for the detection of mechanical injuries in the lumbar spine of a patient and for the identification of these injuries, which method makes use of a new kind of mathematical model of spine applicable to the five lumbar vertebrae and to their disks.

Another object of the invention is to provide an equipment especially designed for carrying out the above mentioned method.

A further object of the invention is to use the method according to the invention for determining the mechanical conditions of the lumbar spine of a patient as an indication to determine the optimal method of rehabilitation of said spine by either a conservative method or a surgical repair.

In accordance with the present invention, it has been noted that any mathematical representation of the anatomy of a spine must include the posterior ligamentous system which has indeed the strength to support any moment generated onto the spine by the body weight and any external load carried by the patient. It has also been noted that the extensors of the hip have the bulk and the lever arm necessary to supply all the moment requirements to flex the spine.

In greater details, it has been noted that, under normal circumstances, most of the motion of an individual flexing forward from zero upright down to about 45° (for an unloaded spine), is due to spinal flexion. From about 45° to full flexion, the motion is mostly due to the rotation of the pelvis at the hips.

In the range of 0° to about 45° (for an unloaded spine), the posterior midline ligament system is inactive and, in its place, the erectores spinae and/or the abdominal muscles support most of the moment due to the body weight. From about 45° to full flexion, this moment can be also supported by the midline ligament system without muscular activity. This relaxation phenomenon from muscular to ligamentous support was already noted in the art by W. F. Floyd et al in their article "The Function of the Erector Spinae Muscles in certain Movements and Postures in Man", J. Physiology, volume 129, pp. 184–203, 1955.

Using electromyographic (EMG) measurements, W. F. Floyd et al clearly saw a relation between the moment to be supported and the angle of forward flexion, and realized the meticulous coordination of muscle, ligament and joint movement. They hypothetized that in the case of injury to an intervertebral joint, this delicate coordination will be upset and this would be reflected in change of the E.M.G. pattern. Then, they embarcated on an E.M.G. study and tried to compare statistically the E.M.G. pattern of normal individuals to that of those with common back problems in the performance to a standardized simple weight lifting task. However, they gave up after testing 140 cases because the results were inconsistent.

The mathematical model used in accordance with the present invention takes it from granted that the pelvis acts as a "supporting base" for entire spine, and assumes as fundamental hypothesis, that any healthy person will perform a task in such a way as to minimize and equalize the stress at each invertebral joint.

In this model, the main power for a lift is assumed to be generated by the extensors of the hip, such as the Gluteus Maximae.

The moment generated by these muscles is transmitted to the upper extremities by the trunk musculature and the posterior ligamentous system (PLS) which, for the purpose of this discussion, is composed of the midline ligament and the lumbodorsal fascia. Regardless of the inclination of the trunk, the moment generated by the extensors of the hip must equal the sum of the moment generated by the trunk musculature and PLS. Therefore, for any given hip extensor moment one can find an infinite number of combinations to distribute this moment between trunk muscles and the PLS.

Because of the reserve capacity in performing a small weight lift, a normal individual may select a combination of ligaments and muscles which is not optimum from a stress minimization and equalization point of view. However, the reserve is reduced in the presence of injury. The option of selecting a non-optimum strategy is also reduced. Therefore one can expect a certain amount of variation in EMG pattern in a normal individual and a very limited variation in those with injury.

Assuming that the distribution of moment between ligaments and muscles is controlled by the requirement that stress be minimized and equalized at all lumbar joints, stress at one intervertebral joint will be defined as the ratio of the resultant compressive force acting perpendicular to the bisector of the disk to the area of the disk. In general, when muscles are used, the stress is higher than when either ligament systems are used, because the lever arms of the ligament systems are longer than those of any of the muscles. The midline ligament system can be activated only when the spine is sufficiently flexed. The hip/shoulder angle $\alpha$ at which this ligament takes up tension is called $\alpha_o$ which is about 45 degrees for no load. This ligament system is strong enough to support the heaviest lift and hence, when this ligament system is activated, the spinal musculature is no longer required and therefore the muscles are electrically silent. As aforesaid, this is the muscle relaxation phenomenon observed by W. F. Floyd et al.

The thoracodorsal fascia can be activated by the contractions of the abdominal muscles, in particular the internal oblique and T. abdominis, which exert a pull at its lateral margin only when the abdominal pressure is at sufficient value to maintain a rounded abdominal cavity. This ligament system can therefore be activated for any angle of flexion. This is an essential difference when compared to the midline ligament.

Based on such a mathematical model, the method according to the invention as claimed hereinafter for the detection of mechanical injuries in the lumbar spine of the patient and the identification of these injuries comprises a basic step of:

(a) providing a mathematical model of spine which is applicable to the five lumbar vertebrae and to their disks and is capable of calculating the distribution of moments, compression and shear forces between the ligaments and muscles at the intervertebral joints of a human being as a function of a load to be pulled up and of the spinal geometry and muscle activity of said human being, said model including the pelvis as a supporting base for the entire spine and assuming, as fundamental hypothesis for its calculation, that any healthy person will perform a task in such a way as to minimize and equalize the stress at each intervertebral joint;

(b) measuring with a set of surface electrodes the electromyographic (EMG) activities of the erectores and abdominals of a patient in a bilateral and symmetrical manner with respect to the spine of said patient while he is flexing forward in the median plane and pulling up a small load;

(c) simultaneously measuring the angle of flexion $\alpha$ of said patient while he is flexing forward, said angle $\alpha$ being the dihedral angle between a plane passing through the hips and shoulders of the patient and a vertical plane parallel to the frontal plane of said patient;

(d) supplying the measured angle $\alpha$ as variable input to the model and running said model with said input to calculate the EMG activities of the erectores and abdominals that would normally be used by a healthy person to produce the same task;

(e) comparing the calculated EMG activities with the EMG activities measured on the patient with the surface electrodes;

(f) tuning parameters of the model to fit the calculated EMG activities to those measured on the patient until their differences are minimized; and (g) detecting and identifying the mechanical injuries, if any, that may be present in the lumbar spine of the patient as a function of the amount and type of tuning that was necessary to complete step (f).

In order to make interpretation easier, the method according to the invention may advantageously comprise the additional steps of:

(h) measuring the lumbo-sacral angle $\lambda$, said angle $\lambda$ being the angle between the bissector of the $L_5$-$S_1$ disc and the bissector of the $T_{12}$-$L_1$ disc of the patient;

(i) determining with said measured angle $\lambda$ the angle $\alpha_o$ at which the lordosis of the patient's spine is eliminated when said patient is pulling up the small load, said angle $\alpha_o$ being the one at which the variation of the rate of change of $\lambda$ versus $\alpha$ is maximum; and (j) using the so determined angle $\alpha_o$ as a parameter meter of interpretation in the mathematical model, said angle $\alpha_o$ indeed corresponding to the angle at which the patient switches the balancing of the load being pulled up from his muscles to his ligaments in order to reduce the stress level which the patient's spine has to sustain.

The equipment according to the invention for use to carry out the above mentioned method comprises:

(a) a mathematical model of spine which is applicable to the five lumbar vertebrae and to their disks and is capable of calculating the distribution of moments, compression and shear forces between the ligaments and muscles at the intervertebral joints of a human being as a function of a load to be pulled up and of the spinal geometry and muscle activity of said human being, said model including the pelvis as a supporting base for the entire spine and assuming, as fundamental hypothesis for its calculation, that any healthy person will perform a task in such a way as to minimize and equalize the stress at each intervertebral joint;

(b) a set of surface electrodes fixable onto the patient in a bilateral and symmetrical manner with respect to his spine for measuring the electromyographic (EMG) activities of the erectores and abdominals of said patient while he is flexing forward in the median plane and pulling up a small load;

(c) means for measuring the angle of flexion $\alpha$ of the patient, said angle $\alpha$ being the dihedral angle between a plane passing through the hips and shoulders of the patient and a vertical plane parallel to the frontal plane of said patient;

(d) means for supplying the measured angle $\alpha$ as variable input to the mathematical model;

(e) means for running the model with its variable input to calculate the EMG activities of the erectores and abdominals that would normally be used by a healthy person to produce the same task;

(f) means for comparing the calculated EMG activities to the EMG activities measured on the patient with the surface electrodes;

(g) means for tuning parameters of the model to fit the calculated EMG activities to those measured on the patient until their differences are minimized; and (h) means for detecting and identifying the mechanical injuries, if any, that may be present in the lumbar spine of the patient as a function of the amount and type of tuning that was necessary to minimize the differences between the calculated and measured EMG activites.

As can be easily understood, the method according to the invention for determining the mechanical condition of the lumbar spine and the extent of breakdown of its mechanism, may be used to classify spines according to their efficiency and thus help in matching jobs with spine conditions to avoid needless exposure to injury, thus reducing the risk of said injury. As a result, the overall cost of medical treatment should be reduced. Moreover, the method according to the invention can be used as a diagnosis tool to determine an optimal method or rehabilitation in the case of an injured spine, by either conservative methods or surgical repair.

The method according to the invention is particularly interesting in that it can be carried out at low cost and thus be used extensively for the screening of individuals with common low back problems in order to diagnose the exact mechanical fault for the purpose of prognostication, treatment, effects of treatment and rehabilitation. The method according to the invention may also be used to assess the individual capacity to perform a given task or, inversally, to assess a particular job for its risk to the individual. It may further be used to assess insurance of risk and compensation and to select fitness or athletic training programs.

It is worth noting again that the mathematical model of spine used in the method and equipment according to the invention assumes, as fundamental hypothesis, that any healthy person will perform a task in such away as to minimize and equalize the stress at each intervertebral joint. In practise, this "stress to be minimized and equalized" can be divided into a plurality of stress components each associated to a given source of stress. Thus, by way of example, the stress may be divided into a compression stress component, a shear stress component, a midline stress component and the like.

In use, it is preferable to take into account all these possible components when defining the stress value to be minimized and equalized. However, in practise, use can be made in prime approximation of one or two of these components only, as fully representative of the whole stress.

BRIEF DESCRIPTION OF THE DRAWINGS

The invention and its advantages will be better understood with reference to the following, non restrictive description of a preferred embodiment thereof, given in connection with the accompanying drawing in which:

FIG. 3(a), (b) and (c) are schematic views of a patient in flexed position and/or of his spine, in which views are defined the angle of flexion $\alpha$, the lumbar curve angle LC and the lumbo-sacral angle $\lambda$;

FIG. 4 (a) is a schematic representation of the relative positions of a strain of markers attached to the skin along the spine in the saggital plate, said markers being used to determine the angle $\lambda$ and $\alpha_o$;

DESCRIPTION OF A PREFERRED EMBODIMENT

A—Theoretical Considerations

As aforesaid, the mathematical model of spine used in the method according to the invention includes the pelvis as a supporting base for the entire spine and assumes as fundamental hypothesis for its calculation, that any healthy person will perform a task in such a way as to minimize and equalize the stress at each intervertebral joint. In other words, all healthy persons are expected to perform a task in such a way as to minimize and equalize the stress at each joint.

Of course, this does not mean that all healthy persons will execute a lift in an identical manner. Differences in individual characteristics will affect the overall response. However, it is essential to understand that the overall response of any healthy individual will reflect the same overall objectives, namely:

(1) lifting the weight; and
(2) minimizing and equalizing the stress at each intervertebral joints.

Because the control system strategy is totally independent of the task, it is reasonable to analyze the problem by selecting a task that will simplify computations and generating enough force at the intervertebral joints to make measurement possible. For this reason, the choice of a weight lifting as a model has been made, although such a choice is not restrictive.

Based on such a choice of a weight lifting, the mathematical model used in the method according to the invention calculates the distribution of moments, compression and shear forces between the ligaments and muscles at the intervertebral joints of the lumbar spine of a human being as a function of the load to be lifted or pulled up and of the spinal geometry and muscles activity of this human being. Originally, the range of motion of the lumbar spine and the measurements required to locate the various muscles and the ligaments were obtained from radiographs. The cross-sectional area of the muscles were obtained from cross-sectional anatomical slices. This allowed the representation of the muscles and ligaments as vector forces with the resultant of all forces estimated as a bissector of the disk. The forces generated by the task were estimated at the line joining the hip and shoulder, the movement of which could be followed in lateral photographs. The forces along this line were then transferred to each of the five lumbar segments.

Using an optimization technique, an objective, criterium function OF defined by its coefficients C1, C2, C3 and C4, was used to calculate the distribution of moments between the ligaments and muscles, which distribution produces a minimum of shear at the bissector of the intervertebral joint. In this feedback hypothesis, the organism monitors the shear and compression forces at the joint and uses this to select the best combination of muscles and ligaments to accomplish a given task. This, in practice, constitutes the control system of the model.

The model used in the method according to the invention makes use of substantially the same function OF. A full description of this mathematical model of spine is given in the Master Engineering Thesis of Albert R. CARBONE which thesis is entitled "A muscular response model the human lumbar spine the performance of a saggital plane dead lift", Concordia University, Montreal, Mar. 1984. In this particular model, the objective function OF to be minimized has the following structure:

OF =C1* (shear) +C2* (comp) +C3* (mid) +C4* (fascia) in which:

C1, C2, C3 and C4 are parameters characterizing the relative importance of each component of the function:

shear is the square of the enclidian norm (SEN) of the shear vector at each joint;

comp is the SEN of the compression vector at each joint;

mid is the SEN of the midline ligament vector at each joint; and fascia is the SEN of the abodminal muscles group vector.

In the above formula, the expression "abdominal muscles" includes the following muscles: external obliques, internal obliques and T. abdominis.

It should be noted that while the hypothesis used in this mathematical model of stress minimization cannot be tested by direct measurements, the deduction from theory can be subjected to experimental verification with certain measurements reported from observations on volunteers performing light tasks.

By way of example, the calculated, integrated E.M.G. value of the sacrospinalis and the multifidus muscles are disclosed in the litterature as being substantially linear for a range of weight listed from 0 to 40 kg. This linear relationship also exists in the model used in the method according to the invention. In addition, it has been found that by using an appropriate conversion factor, the muscle activity calculated with the spine model according to the invention can be superimposed on the experimental data.

In the litterature, it is also disclosed that there is a linear relationship between the disk pressure and the weight supported by the spinal column in the case of a small weight. This finding is confirmed with the calculation of the mathematical model used in accordance with the invention.

Similar correlations can be obtained between the calculated values of the abdominal pressure, the moment of directores and the angle of spine flexion at which the midline ligament is first brought under tension, and the data collected in the litterature.

As a result, it may be taken for granted that the unique response of the mathematical model used in accordance with the invention actually reflects the basic relationship between the various components of the spine system of a human being. This basic relationship relates the stress distribution to the size and shape of the structural units composing the individual spine. It also takes into consideration the degree of lumbar curve, the elasticity of a ligamentous structure and the firing density of contractile muscles.

It should be noted that in the mathematical model used in accordance with the invention, a physiological loading system is yielded, where the resultant force is always substantially maintained at 90° to the bissector of the disk. This allows the conclusion that the facets, despite current teaching, take negligible compression load because they are oriented at 90° to the bissector of the disk. However, the facet joints and the disk are responsible for supporting all the shear stresses.

Asymmetry of an intervertebral joint may reflects an asymmetric shear stress and the degree of asymmetry reflects the differences in shear stress between right and left sides of the joint. The disk does not have the structural design to support shear stress. The obvious protective mechanism would be (1) asymmetric facet joint and (2) asymmetric muscular response.

With an increased load, a change in the fixed structure cannot be expected and therefore the only protective mechanism would be an asymmetric muscle response small at low loads, but increasing with the magnitude of the task. It is known that the compensation is not perfect because of the asymmetric degeneration found in asymmetric joints. Therefore, there is a weight range where the compensation works and, outside of this, it does not.

In practise, the differences in E.M.G. output between right (R) and left (L) sides are due to a variety of factors such as the skin resistance, variability of muscle motor points and asymmetry. In there were no asymmetry, then R should be equal to L. But factors other than asymmetry introduce a difference between R and L. If we assume that there is a constant gain difference between R and L because of asymmetric structure, then this difference can be identified. The R and L integrated output is collected at each millisecond. The sum of the square of all $(R-aL)$ is obtained and minimized with respect to "a". The value of this parameter "a", which in the ideal case of perfect symmetry is equal to one, characterizes the irreducible asymmetry between R and L and is arbitrarily assigned to describe the asymmetry of the joint.

As a first approximation, the small contribution of the disk to the support of shear force is ignored. Now, if it is true that stress if equalized, then the geometrical differences between right and left facets must be reflected in the differences in E.M.G. output of the two sides. The shear induced by bodyweight and muscles in the asymmetric joint will induce a torque which must be compensated by the size and distribution of the facets joints. The bodyweight and muscles contribution to shear stress $(R+L)$ can be calculated. The moment produced by muscles must be sufficient to balance bodyweight in relaxed upright stance.

When an external load is added, it becomes more difficult for the facet joints to absorb the increased asymmetric stress. The torque at the IV joint is increased and the joint tends to rotate. To compensate, an asymmetric muscle response is required.

The simple joint model thus proposed relates EMG activity and joint asymmetry to the shear component of stress induced by an axial compression load. This joint model is particularly interesting in that it obviates the need for complex IV joint models.

B—Equipment

Figure 1:
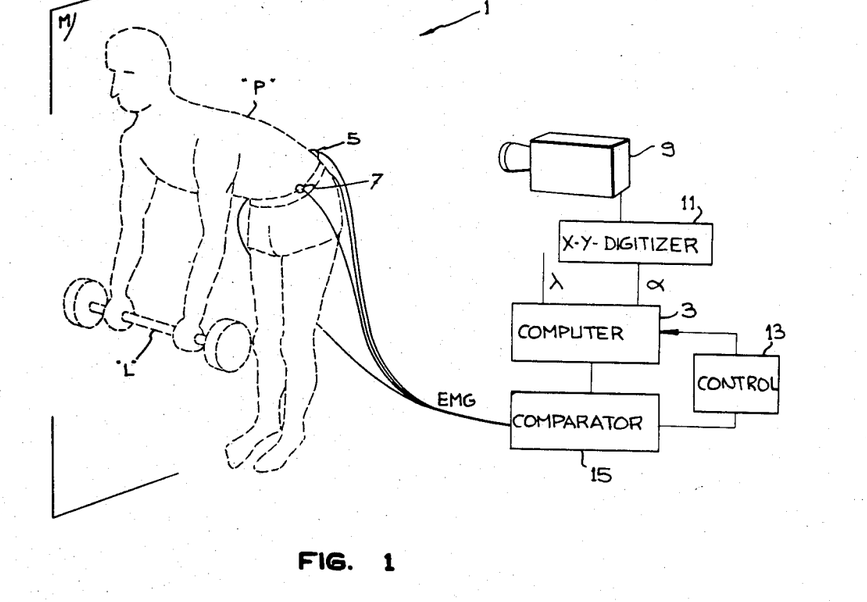
FIG. 1 is a schematic view of a non-invasive equipment for the detection of mechanical injuries in the lumbar spine of the patient and the identification of these injuries.

As shown in FIG. 1, the equipment 1 necessary for the detection of mechanical injury in the lumbar spine of a patient P and for the identification of the so detected injuries comprises a computer 3 preprogrammed with the above mentioned mathematical model of spine applicable to the five lumbar vertebrae of the patient B and to their disk. As computer 3, use can be made of a standard IBM-PC or HP-9000 computer (trademark). The equipment 1 also comprises a first set of surface electrodes 5 fixable onto the patient P in a bilateral and symmetrical manner with respect to his spine for measuring the electromyographic activities of the erectores (sacrospinalis, multifidus, etc...) of this patient while he is flexing forward in his median plane M and pulling up a small load L. The load to be pulled up may consist of a small weight to be lifted up, as shown in FIG. 1, or of a mere chain or elastic strip fixed to the ground. The equipment 1 also comprises another set of surface electrodes 7 fixable onto the patient P in a bilateral and symmetrical manner with respect to his spine for measuring the electromyographic activities of the abdominals of said patient while the same is flexing forward in the median plane and pulling up the small load L. Advantageously, these electrodes 7 may fixed onto the triangles of Petit of the patient P in order to record the EMG activities of the internal oblique of said patient. In this particular case the so recorded activities can be used as an indicative value of the activity of all of the abdominals.

Figures 3A, 3B, 3C:
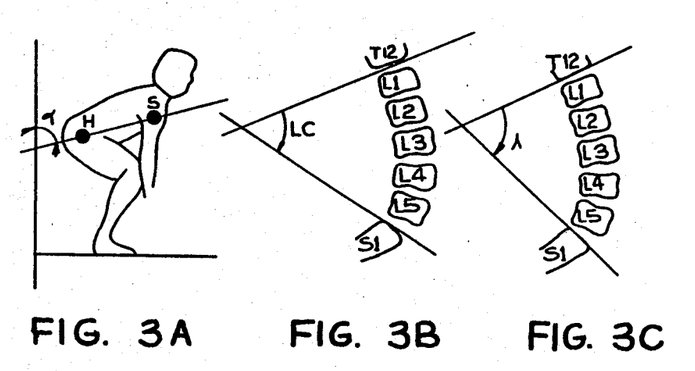

Means including a stop-action camera 9 are used for measuring the angle of flexion $\alpha$ of the patient, the angle $\alpha$ being the dihedral angle between a plane passing through the hips and shoulders of the patient and the vertical plane parallel to the frontal plane of said patient (see FIG. 3a). The stop-action camera 9 is connected to an X-Y digitizer 11 for digitizing the relative positions of the shoulders and hips of the patient in the median plane. As camera 3 and X-Y digitizer 11, use can be made of a standard digitizing camera system such as those sold by NORTHERN DIGITAL of Waterloo (Ontario), SELSPOT of Sweden or VICOM of the United States. Of course, such a system has to be connected to the computer by a standard interface system. The digitizer 11 is connected to means known per se for determining the angle $\alpha$ between a line passing through the digitized positions and a vertical line. In practice, these means for determining $\alpha$ may be included into the computer 3, as schematically illustrated in FIG. 1.

A standard panel or keyboard 13 provided by the computer's manufacturer is used for operating the computer 3 and running the model with the angle $\alpha$ which is supplied to it as a "variable input" together with the load L, in order to calculate the EMG activities of the erectores and abdominals that would normally be used by a healthy person to produce the task of pulling up the load L. The so calculated EMG activities are supplied to a comparator 15 wherein they are compared to the EMG activities measured on the patient P with the surface electrodes 5 and 7. This comparator may be external to the computer but is preferably "incorporated" thereto as a software routine.

Either automatically or manually, the parameters $C_1$ to $C_4$ of the mathematical model preprogrammen in the computer 3 may be tuned using the control panel 13, to fit the calculated EMG activities to those measured on the patients until their differences are minimized. When the latter operation is completed, the amount and type of tuning that was necessary to carry out with the control panel 13 can be used as "means" for detecting and identifying the mechanical injuries if any, that were present that the lumbar spine of the patient.

Figure 2:
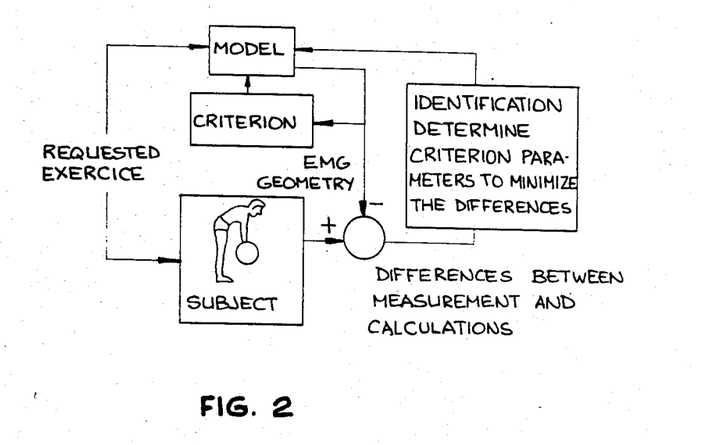
FIG. 2 is a schematic representation of the identification procedure.
Figure 9:
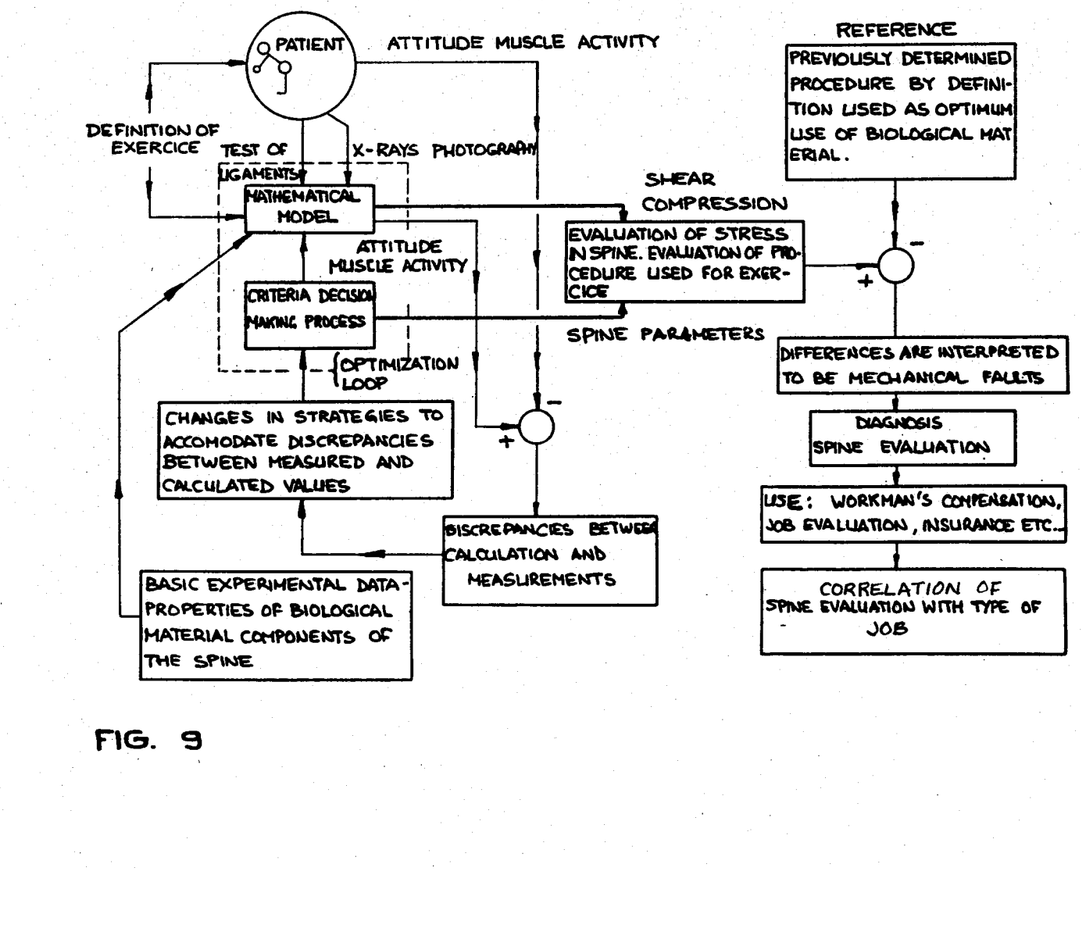
FIG. 9 is a flow-chart of the model according to the invention, with reference to its possible use.

A detailed block diagram of the method according to the invention, making use of the above referenced equipment, is given in FIGS. 2 and 9.

C—COLLECTION AND TREATMENT OF THE INFORMATION (a) Determination of the EMG activities versus the angle of flexion $\alpha$ After fixation of the surface electrodes 5 and 7 onto the erectores and abdominals of the patient P in a bilateral and symmetrical manner with respect to his spine, the patient P is requested to execute a simple weight lifting symmetrical task with the load L which is preferably lower than 10 kg. During the lift, the EMG activity is monitored as explained hereinabove, together with the attitude of the patient.

The EMG signals are bandpass analog filtered in the range of 10 to 300 Hz and then digitized at 1,000 samples per second (12 bits accuracy) and stored on-line on digital disks. When the task is complete, the data is available for recall and processing. The artifacts may be routinely reduced and the data smoothed by using a combination of linear and non linear filtering algorithms. This gives an envelope of the measured muscle activity as a function of time. Of course, a greater degree of sophistication is possible because, in this particular case, the theory predicts the shape and form of EMG signals. Use can be made of this information to define more accurately the true muscle response.

As explained hereinabove, the attitude of the patient is synchronized with the acquisition of EMG data by using the stop-action camera 9 at four frames per second. The marked positions of the shoulders and hips are digitized with the X-Y digitizers 11. This procedure permits to obtain the EMG at any hip-shoulder attitude, which is defined by the angle $\alpha$. The skin motion has a negligeable effect on the determination of the angle $\alpha$.

Figure 5A:
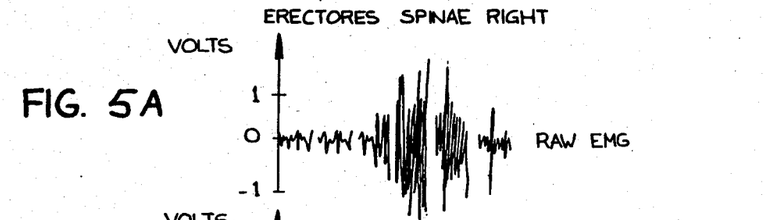
FIGS. 5(a) and (b) are non-processed and processed E.M.G. signals of the erectores spinae of a patient versus time.
Figure 5B:
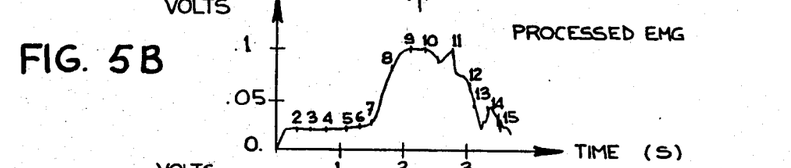
Figure 5C:
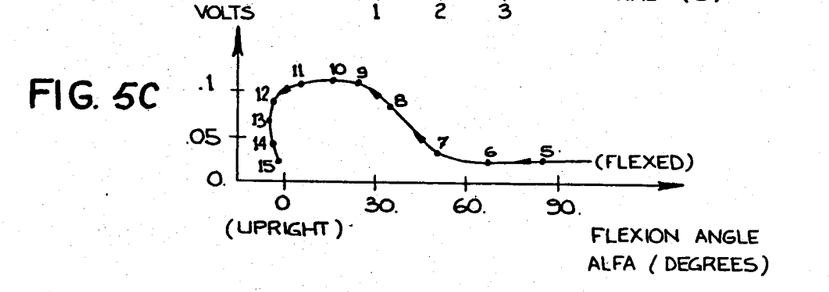
FIG. 5(c) is a representation of the processed E.M.G. signal of FIG. 5(b) versus $\alpha$.

A typical measurement of EMG and its subsequent processing is shown in FIGS. 5(a), (b), (c). In FIG. 5(a) the EMG of the erectores spinae is shown versus time. This particular case, the signal was band-filtered and amplified between 10 and 300 Hz. The measuring electrode was located at the level of vertebra $L_3$ at 5 cm to the right of the spineous process of the vertebra.

FIG. 5(b) shows the processes EMG signal versus time. The numbers superimposed onto the curve indicates the instant at which photographs were taken. This permits the measurement of the flexion angle $\alpha$.

Last of all, FIG. 5(c) shows the processed EMG activity versus $\alpha$. This FIG. 5(c) clearly shows that, from zero 45°, the external moment in the lumbar zone is balanced by the action of the muscles. During this first arc of motion, the spine unfolds or straightens out. At approximatively 45° the spine is sufficiently flexed to permit the midline ligament to be set under tension. When this is done, the power of the hip extensors is transmitted directly to the upper extremities. In this particular case, there is no more need for an activity of the erectores spinae.

It can be appreciated that a stiff spine will not permit the full use of the posterior ligamenteous system instead of the erectores spinae. Consequently, the erectores spinae would have to work more and therefore increase the level of stress that the spine must take with the attendant higher probability of failure.

It should also be noted that in calculating EMG patterns, the mathematical model can use the average data from the right and left electrodes for each group of muscles.

(b) Measurement of the lumbo sacral curve angle

As aforesaid, an healthy individual naturally switches the balancing of a load from his muscle to his ligaments in order to reduce the stress level which his spine has to sustain. As such a switch-over cannot be executed until the midline ligaments are set under tension, it may be of great interest to know the precise time at which such a switch-over occurs in order to better interpret the EMG data. It is therefore of great interest to determine the angle of flexion $\alpha_o$ at which the spine is sufficiently flexed for the midline to be activated.

Preliminary investigation conducted by the inventor as shown that $\alpha_o$ is a function of the weight to be lifted. The same investigation has also shown that, when the weight to be lifted is small, the individual has considerable freedom in determining at which point it will switch over from muscles to ligaments. This is due to the fact that the midline ligaments can be set under tension by a combination of spine flexion and pelvis rotation.

As the hip-shoulder angle $\alpha$ does not describe this particular combination, it is difficult to obtain $\alpha_o$ simply by monitoring $\alpha$, in view of subsequently supplying this $\alpha_o$ to the mathematical model in order to permanently construct a new data base for every individual being tested. The determination of $\alpha_o$ must therefore be made separately and this can be done in practise as follows.

According to a first invasive method, the determination of $\alpha_o$ can be accomplished by measuring the change in lumbar spine rotation in lateral radiographs between upright relaxed stance and full forward relaxed flexion. The sacro-lumbar curve referred to hereinabove is the angle LC shown in FIG. 3(b) between the lower end plate of vertebrae $T_{12}$ and the upper end plate of vertebra $S_1$. Geometrical considerations dictate that the sacro-lumbar curve angle depends on the ligament length. Because the midline ligament is a passive structure, its length is determined by the tension it has to sustain, provided that this tension is not maintained for a long time. Therefore, the sacro-lumbar curve angle LC characterized the ligament tension. As the subject lift a weight, the sacro-lumbar angle increases slowly until the tension of the midline ligaments drops to zero. From them on, the sacro-lumbar curve increases rapidly. The sudden change in sacro-lumbar curve marks the $\alpha_o$ angle.

Figure 4A:
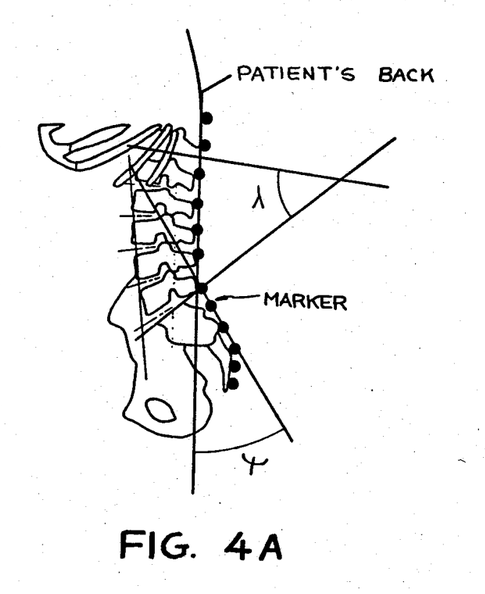
Figure 4B:
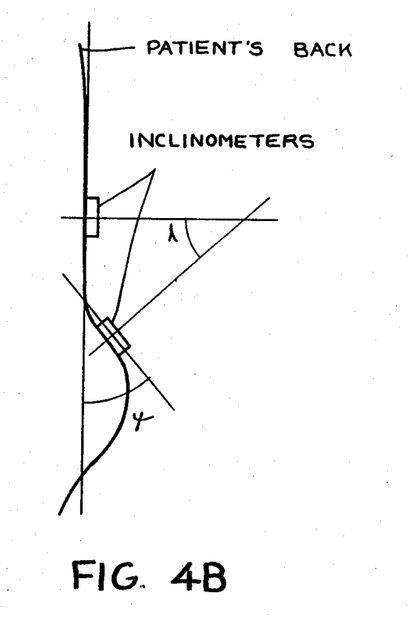
FIG. 4(b) is a schematic representation of the relative positions of two inclinometers attached to the skin along the spine in the saggital plane, said inclinometers being used to determine the angle $\lambda$ and $\alpha$.

In a second non-invasive method, the lumbo-sacral angle $\lambda$ can be measured in a non-invasive manner by detachably fixing a string of skin markers to the skin of the back of the patient in the midline of his spine from at least thoracic vertebra $T_{10}$ down to at least sacral vertebra $S_3$ (see FIG. 4). The skin markers may consist of visible dots, in which case their relative positions may be monitored with a high resolution TV camera. Alternatively, they may consist of ultrasonic emitters, in which case their relative positions may be monitored with a set of three ultrasonic microphones. According to a third method, the skin markers may consist of small reflectors in which case a laser beam may be used as visualisation equipment.

In all cases, when the individual flexes forward, the skin markers move with the corresponding change in the lumbo-sacral angle $\lambda$. Mathematical curve fitting allows the identification of the inflexion point on the curve. By tracing tangents to this inflexion point, it is possible to determine an angle $\psi$ between said tangents, which angle $\psi$ is directly related to the lumbo-sacral angle $\lambda$ (see FIG. 4).

This dynamic technique of angle determination is the relatively insensitive to change in skin markers relative to the underlying bony landmarks. The markers stay in the midline as they move with the skin along the main axis of the spine and therefore skin motion in this direction is not important in the determination of the angle. Displacements in the saggital plane between markers and bony points could make a difference at the sacro-lumbar joint where there is a greatest thickness of interposed fat. However, it is in this region that the saggital plane displacement of markers create the last error in the angle determination.

In practice, the angle $\psi$ may be used directly instead of the lumbo-sacral angle $\lambda$, since the present invention is only concerned with timing and not with absolute values.

In accordance with a third, non-invasive method the measurement of $\alpha_o$ can be carried out by pressing a pair of inclinometers against the lumbar spine of the patient. By measuring with these inclinometers the range of motion of the spine (ROMS) and the range of motion of the pelvis (ROMP) when the patient is flexing forward, it is possible to determine the lumbo-sacral angle $\lambda$. Indeed, as the subject flexes forward, the ROMS varies at the spine straightens. When the spine is straight, the ROMS stops varying, although $\alpha$ continues to vary (because the subject continues to bend forward since his pelvis rotates). The value of $\alpha$ at which ROMS stops varying defines the angle $\alpha_o$. This particular way of determining the angle $\lambda$ and deriving therefrom the angle $\alpha_o$ is disclosed by T. G. Mayer et al in their article "The use of non-invasive techniques for quantification of spinal range of motion in normal subjects and chronic low back dysfunction patient", Spine, volume 9, No. 6, 1984, pp 588 to 595.

As explained hereinabove, the measurement of the lumbo-sacral angle $\lambda$ permits to obtain the angle $\alpha_o$ at which the lordosis of the patient's spine is eliminated when the patient is pulling up the small load, said angle $\alpha_o$ being the one at which the variation of the rate of change of $\lambda$ vs $\alpha$ is maximum.

As also indicated hereinabove, the so determined angle $\alpha_o$ can be used as a parameter interpretation in the mathematical model, said angle $\alpha_o$ indeed corresponding to the angle at which the patient will switch the balancing of the load being pulled up from his muscles to his ligaments in order to reduce the stress level which his spine has to sustain.

(c) Treatment of the information

Once the mathematical model of spine has been provided for, it is of course necessary to supply it with a data base for use as a reference to construct a proper model for every patient to be tested. The creation of this data base reference can be made by using the average response of a group of persons without clinically observed symptoms that can be referred to back problems. Identification procedure executed on every member of this particular group will generate a set of parameters C1, C2, C3 and C4 for each member, thereby providing the range of variation of said parameters for anybody "clinically" normal.

After fixation of the electrodes 5 and 7 to the patient P in a bilateral and symmetrical manner with respect to this spine and connection of these electrodes to the comparator 15 itself connected to the computer 3 and to the control panel 13, the patient will be asked to pull up the small load L while measuring its angle of flexion $\alpha$ and, if necessary, his lumbo-sacral angle $\lambda$. The information supplied to the computer 3 preprogrammed with the mathematical model, which information includes the load L, the angle $\alpha$ and the sacro-lumbar angle $\lambda$ used for calculating $\alpha_o$, will allow the computer 3 to calculate the muscle forces which are corrected to reflect the muscle length only, since the task is executed at low speed. This gives a calculated EMG pattern indicative the activities of the erectores and the abdominals that would normally be used by a healthy person to produce the same task.

This calculated EMG pattern will then be supplied to the comparator 15 where it will be compared with the corresponding EMG activities measured directly onto the patient with the electrodes 5 and 7. The output signal of the comparator 15 is supplied to the control panel 13 which, in turn, acts onto the computer 3 to tune the values of the parameters C1, C2, C3 and C4 to fit the calculated EMG pattern to be observed one, until their differences are minimized (see FIG. 2).

When it is achieved, any mechanical injury present in the spine of the patient P lifting the weight L, will be easily detected and identified as a function of the amount and type of tuning that was necessary to minimize the differences between the calculated and measured EMG activities.

(i) Healthy response

A healthy response that can be obtained from a patient lifting a small load is variable as shown in FIG. 7 which shows healthy EMG responses as a function of different loads to be lifted (10, 15, 20 and 25 kg). The consistency of each set of curves shown in FIG. 7 is evidence that the subject controls the share of moment supported by the muscles. Curves (A) show an early extensor shut off. The spine flexes as soon as possible. Curves (B) show a late extensor shut-off. In this case, the spine flexion is delayed as long as possible. Curves (C) show an intermediate strategy. Last of all, curves (D) is an overlay of curves A, B and C for a 25 kg load. As can be seen, the muscle relaxation phenomena and the variation of the switch-over from muscle to ligament are evident and not scatter.

The mathematical model used in the method according to the invention permits to explain such a variation as due to the controlled delay in setting up the ligament tension. As explained hereinabove, this is expected when the loads are low.

Figure 6:
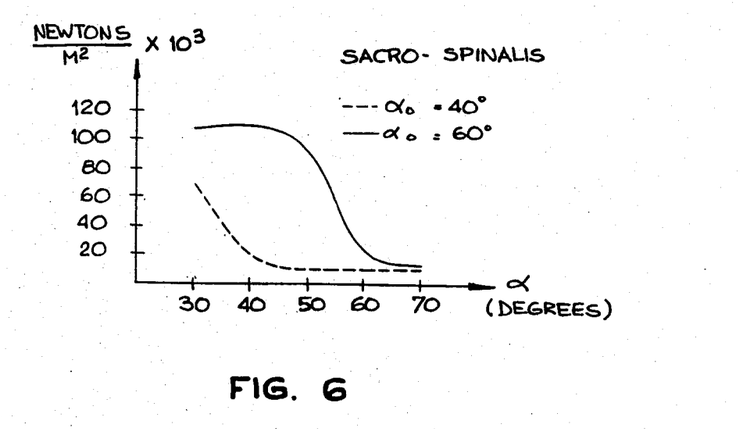
FIG. 6 is a simulation of the E.M.G. response for two different values of the sacro-lumbar curve angle LC controlling the switch-over from muscle to ligament.
Figure 7A:
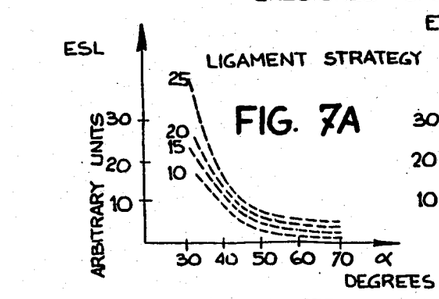
FIGS. 7(a) to (c) are representation of a healty E.M.G. response of the left erectores spinae of the patient as a function of the load to be lifted in the case of an early extensor shut-off, a late extensor shut-off and an intermediate strategy, respectively.
Figure 7B:
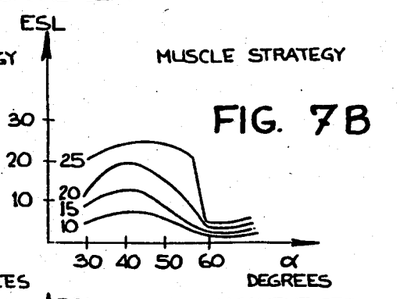
Figure 7C:
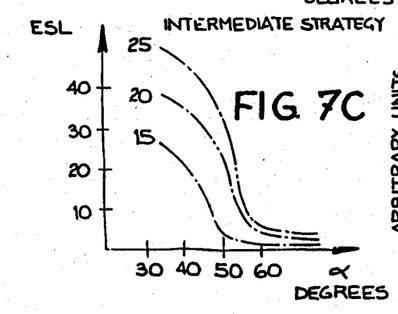
Figure 7D:
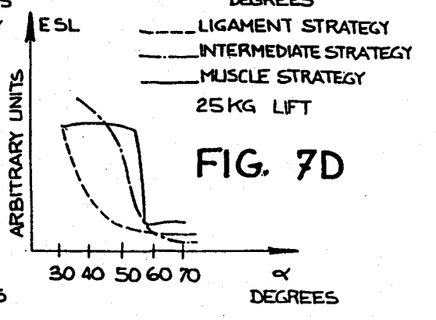
FIG. 7(d) is an overlay representation of the curves shown in FIGS 7(a) to (c) for a 25 kg load.

The apparent variation in the EMG pattern is due to the ability of the individual to alter his pelvis angle in order to control the angle flexion at which the ligaments are introduced. The theory relates the onset of ligaments tension to the lumbo-sacral angle $\lambda$. Hence, the variation noted is not true scatter and does not represent a true variation in spine mechanics. This behaviour can indeed be simulated by the model, as shown in FIG. 6 which is a simulation of the EMG responses in the case of two differents values of the sacro-lumbar curve angles to which correspond a given angle $\alpha_o$ at which switch-over occurs from muscles to ligaments;

(ii) Abnormal response

An abnormal response is substantially different from a normal one in several respect. First, the degree of symmetry in the data collected by the right and left electrodes is poor. Secondly, the spine is not completely flexed, such being apparent from the fact that the erectores are active until the weight is on the floor. Third, the variation is muscular response during the lift is not smooth.

Figure 8A:
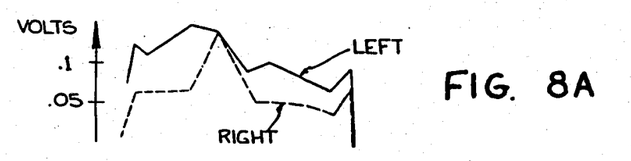
FIG. 8(a) to (c) are examples of abnormal E.M.G. responses.
Figure 8B:
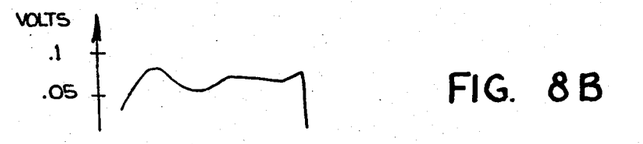
Figure 8C:
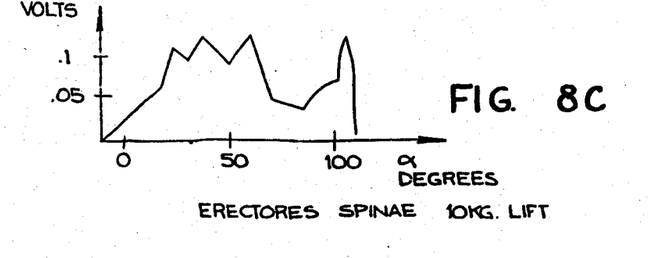

FIG. 8 gives examples of such abnormal responses. More particularly, FIG. 8 (A) shows an assymetric response. FIG. 8(B) shows a response in the case of a lack of muscle relaxation. FIG. 8(C) shows an irregular response (see, by way of comparison, FIG. 5(C)).

As can now be easily understood, the ability to identify the control system of an individual combined with the kinematics of a symmetrical task such as a symmetrical weight lifting advantageously permits:

the assessment of the stress induced by a task on an individual, as a function of the amount of tuning necessary to minimize the differences between the observed and calculated pattern;

the observation of an individual on different occasions over a period of time; and the detection of injury and state of recovery;

the identification of the type of injury;

the amount of stress induced by any given task.

It should be noted that the basic anthropometric measurement of the patient to be tested can also be supplied as input to the model. The major anthropometric measurements are the location of the center gravity of the upper body relative to the lumbo-sacral joint and the distance between the hip and the shoulder, and the body weight. A model may of course be scaled to these measurement. It should however be noted that, in practice, individual variation may have no important effect on the control system, if test procedure is uniforming and simplified. It may therefore become no longer necessary to record the weight and the height of an individual and even to mesure the angle $\alpha$ provided that the task is standardized.

Although the masculine pronoun has been used exclusively hereinabove, it has to be interpreted as including the feminine.

I claim:

1. A method for the detection of mechanical injuries in the lumbar spine of a patient and the identification of said injuries, comprising the steps of:

(a) providing a mathematical model of spine which is applicable to the five lumbar vertebrae and to their disks and is capable of calculating the distribution of moments, compression and shear forces between the ligaments and muscles at the intervertebral joints of a human being as a function of a load to be pulled up and of the spinal geometry and muscle activity of said human being, said model including the pelvis as a supporting base for the entire spine and assuming, as fundamental hypothesis for its calculation, that any healthy person will perform a task in such a way as to substantially minimize and equalize the stress or an approximation thereof at each intervertebral joint;

(b) measuring with a set of surface electrodes the electromyographic (EMG) activities of the erectores and abdominals of a patient in a bilateral and symmetrical manner with respect to the spine of said patient while he is flexing forward in the median plane and pulling up a small load;

(c) simultaneously measuring the angle of flexion $\alpha$ of said patient while he is flexing forward, said angle $\alpha$ being the dihedral angle between a plane passing through the hips and shoulders of the patient and a vertical plane parallel to the frontal plane of said patient;

(d) supplying the measured angle $\alpha$ as variable input to the model and running said model with said input to calculate the EMG activities of the erectores and abdominals that would normally be used by a healthy person to produce the same task;

(e) comparing the calculated EMG activities with the EMG activities measured on the patient with the surface electrodes;

(f) tuning parameters of the model to fit the calculated EMG activities to those measured on the patient until their differences are minimized; and (g) detecting and identifying the mechanical injuries, if any, that may be present in the lumbar spine of the patient as a function of the amount and type of tuning that was necessary to complete step (f).

2. The method of claim 1, wherein the measurement of $\alpha$ is carried out by:

monitoring and recording with a stop-action camera the relative positions in the median plane of the shoulders and hips of the patient while the same is bending forward;

digitizing with an X-Y digitizer said relative positions;

determining the angle between a line passing through said digitized positions and a vertical line; and
using the so determined angle as angle $\alpha$.

3. The method of claim 2, wherein the relative positions of the shoulder and hips are monitored at least twice per second.

4. The method of claim 2, comprising the additional steps of:
(h) measuring the lumbo-sacral angle $\lambda$, said angle $\lambda$ being the angle between the bissector of the $L_5-S_1$ disc and the bissector of the $T_{12}-L_1$ disc of the patient;
(i) determining with said measured angle $\lambda$ the angle $\alpha_o$ at which the lordosis of the patient's spine is so reduced that the midline ligament is activated when said patient is pulling up the small load, said angle $\alpha_o$ being the one at which the variation of the rate of change of $\lambda$ versus $\alpha$ is maximum; and
(j) using the so determined angle $\alpha_o$ as a parameter of interpretation in the mathematical model, said angle $\alpha_o$ indeed corresponding to the angle at which the patient switches the balancing of the load being pulled up from his muscles to his ligaments in order to reduce the stress level which the patient's spine has to sustain.

5. The method of claim 4, wherein the measurement of $\lambda$ is carried out in a non-invasive manner by:
detachably fixing a string of skin-markers to the skin of the back of the patient in the midline of his spine from at least thoracic vertebra $T_{10}$ down to at least sacral vertebra $S_3$;
monitoring with a high resolution T.V. camera the relative positions of said skin-markers in the median plane of the patient while the same is flexing forward, said skin-markers altogether defining a curve with an inflexion point;
locating the inflexion point on the monitored curve and tracing tangents to said inflexion point;
measuring the angle $\psi$ between said tangents; and using said angle $\psi$ as angle $\lambda$.

6. The method of claim 4, wherein the measurement of $\lambda$ is carried out in a non-invasive manner by:
pressing a pair of inclinometers against the lumbar spine of the patient;
measuring with said inclinometers a range of motion of the spine (ROMS) and a range of motion of the pelvis (ROMP) when the patient is flexing forward; and
deriving from said ranges the lumbo-sacral angle $\lambda$.

7. The method of claim 4,
wherein the mathematical model provided for in step (a) makes use of a criterion function (OF) to be optimized and minimized when the model is run, said function (OF) having the following structure:

OF =C1* (shear) +C2*(comp) +C3*(mid) +C4* (fascia) in which:
C1, C2, C3 and C4 are parameters characterizing the relative importance of each component of the function:
shear is the square of the enclidian norm (SEN) of the shear vector at each joint;
comp is the SEN of the compression vector at each joint;
mid is the SEN of the midline ligament vector at each joint; and
fascia is the SEN of the abdominal muscles group vector; and wherein the parameters to be tuned in step (f) are the parameters C1, C2, C3 and C4 of function (OF).

8. An equipment for the detection of mechanical injuries in the lumbar spine of a patient and the identification of said injuries, comprising:
(a) a programmed computer containing, in its programm, a mathematical model of a spine which is applicable to the five lumbar vertebrae and to their discs and is capable of calculating the distribution of moments, compression and shear forces between the ligaments and muscles at the intervertebral joints of a human being as a function of a load to be pulled up and of the spinal geometry and muscle activity of said human being, said model including the pelvis as a supporting base for the entire spine and assuming, as fundamental hypothesis for its calculation, that any healthy person will perform a task in such a way as to substantially minimize and equalize the stress or an approximation thereof at each intervertebral joint;
(b) a set of surface electrodes fixable onto the patient in a bilateral and symmetrical manner with respect to his spine for measureing the electromyographic (EMG) activities of the erectores and abdominals of said patient while he is flexing forward in the median plane and pulling up a small load;
(c) means for measuring the angle of flexion $\alpha$ of the patient, said angle $\alpha$ being the dihedral angle between a plane passing through the hips and shoulders of the patient and a vertical plane parallel to the frontal plane of said patient;
(d) means connected to the computer for supplying the measured angle $\alpha$ as variable input to the mathematical model;
(e) means for forming part of the computer for running the model with its variable input to calculate the EMG activities of the erectores and abdoninals that would normally be used by a healthy person to produce the same task;
(f) means for comparing the calculated EMG activities to the EMG activities measured on the patient with the surface electrodes; and
(g) means for tuning parameters of the model to fit the calculated EMG activities to those measured on the patient until their differences are minimized;
whereby any mechanical injuries that may be present in the lumbar spine of the patient is detected and identified as a function of the amount and type of tuning that was necessary to minimize the differences between the calculated and measured EMG activities.

9. The equipment of claim 8, wherein said means for measuring the angle of flexion $\alpha$ comprises:
a stop action camera for monitoring, in the median plane, the relative positions of the shoulders and hips of the patient when the same is bending forward;
an X-Y digitizer for digitizing said relative positions; and
means forming part of the computer programm for determining the angle between a line passing through said digitized positions and a vertical line, said determined angle being used as angle $\alpha$.

10. The equipment of claim 9, further comprising:
(i) means for measuring the lumbo sacral angle $\lambda$, said angle $\lambda$ being the angle between the bissector of the $L_5-S_1$ disc and the bissector of the $T_12-L_1$ disc of the patient;

(j) means forming part of the computer programm for determining the angle $\alpha_o$ at which the lordosis of the patient's spine is eliminated when said patient is pulling up a small load, said angle $\alpha_o$ being the one at which the variation of the rate of change of $\lambda$ versus $\alpha$ is maximum; and (k) means forming part of the computer programm for supplying said angle $\alpha_o$ as an interpretation parameter to the mathematical model.

11. The equipment of claim 10, wherein said means for measuring the lumbo sacral angle $\lambda$ comprises:

a plurality of skin-markers attachable to the skin of the back of the patient to form a string along the midline of his spine from at least thoracic vertebra $T_10$ down to at least sacral vertebra $S_3$;

a high resolution T.V. camera for monitoring the relative positions for said skin-markers in the median plane of the patient while the same is flexing forward, said skin-markers all together defining a curve with an inflexion point;

means forming part of the computer programm for locating the inflexion point on the monitored curve;

means forming part of the computer programm for tracing tangents to said inflexion point; and means forming part of the computer programm for measuring the angle $\psi$ between said tangents, said angle $\psi$ between said tangent being used as angle $\lambda$.

12. The equipment of claim 10, wherein said means for measuring the lumbo sacral angle $\lambda$ comprises:

a pair of inclinometers to be pressed against the lumbar spine of the patient;

means for measuring with said inclinometers a range of motion of the spine (ROMS) and a range of motion of the pelvius (ROMP) when the patient is flexing forward; and means forming part of a computer programm for deriving from said ranges the lumbo-sacral angle $\lambda$ of the patient.

13. The equipment of claim 8 wherein the mathematical model comprises a criterion function (OF) to be optimized and minimized when the model is run, said function (OF) having the following structure:

$$OF = C1*(shear) + C2*(comp) + C3*(mid) + C4*(fascia)$$

in which:

C1, C2, C3 and C4 are parameters characterizing the relative importance of each component of the function;

shear is the square of the enclidian norm (SEN) of the shear vector at each joint;

comp is the SEN of the compression vector at each joint;

mid is the SEN of the midline ligament vector at each joint; and fascia is the SEN of the abdominal muscle group vector; and wherein the parameters to be tuned in step (g) are the parameters C1, C2, C3 and C4 of function (OF).

* * * * *